United States Patent [19]
Gardner et al.

[11] Patent Number: 5,405,404
[45] Date of Patent: Apr. 11, 1995

[54] INSTRUMENT FOR DISASSEMBLING A BIPOLAR HIP PROSTHESIS

[75] Inventors: Kenneth J. Gardner, Roundrock; Adriana de la Barcena, Austin; Steven L. van der Meulen, Cedar Park; Donald W. Dye, Pflugerville; Amber E. Okoye; Mark L. Arlitt, both of Austin, all of Tex.

[73] Assignee: Intermedics Orthopedics, Inc., Austin, Tex.

[21] Appl. No.: 133,743

[22] Filed: Oct. 7, 1993

[51] Int. Cl.⁶ ............................................. A61F 2/34
[52] U.S. Cl. ...................................... 623/23; 623/22; 606/99
[58] Field of Search .................... 606/99, 100, 91, 86, 606/53; 623/22, 23; 411/386, 408, 411, 378, 427, 429, 497, 493, 439

[56] References Cited
U.S. PATENT DOCUMENTS

| | | | |
|---|---|---|---|
| 1,394,608 | 10/1921 | Davern | 411/386 |
| 2,826,631 | 3/1958 | Rohe | 411/427 |
| 3,156,152 | 11/1964 | Reed | 411/386 |
| 3,180,202 | 4/1965 | Kahn | 411/386 |
| 4,170,918 | 10/1979 | Burge | 411/427 |
| 4,470,736 | 9/1984 | Tasseron | 411/404 |
| 4,686,971 | 8/1987 | Harris et al. | 606/99 |
| 4,716,894 | 1/1988 | Lazzeri et al. | 606/91 |
| 4,834,081 | 5/1989 | Van Zile | 606/99 |
| 5,059,196 | 10/1991 | Coates | 606/99 |
| 5,061,270 | 10/1991 | Aboczky | 606/91 |
| 5,073,073 | 12/1991 | Kazino et al. | 411/386 |
| 5,116,339 | 5/1992 | Glock | 606/91 |
| 5,169,399 | 12/1992 | Ryland et al. | 606/91 |
| 5,209,622 | 5/1993 | Kazino et al. | 411/386 |
| 5,236,433 | 8/1993 | Salyer | 606/91 |
| 5,264,680 | 11/1993 | Seibold et al. | 219/227 |

Primary Examiner—Stephen C. Pellegrino
Assistant Examiner—Guy V. Tucker
Attorney, Agent, or Firm—Richard L. Robinson

[57] ABSTRACT

An apparatus for disassembling a head and acetabular component of a bipolar orthopedic hip prosthesis. The head includes a female taper configured for engaging a corresponding male taper of a femoral component of a hip prosthesis. The acetabular component includes a cavity in which the head is elastically constrained. The apparatus includes a rod having a male taper at one end thereof sized and configured to be received in taper locking engagement in the female taper of the head of the bipolar prosthesis. The rod has external threads that engage internal threads of a sleeve surrounding the rod. The sleeve includes a thrust surface at one end that engages the acetabular component as the sleeve is rotated relative to the rod. The sleeve causes the acetabular component to be pressed off of the head while the head remains taper locked to the rod. Continued rotation of the sleeve causes the head to be pressed off of the taper of the rod. A handle attached to the rod facilitates gripping the rod and preventing its rotation while the sleeve is being rotated.

8 Claims, 2 Drawing Sheets

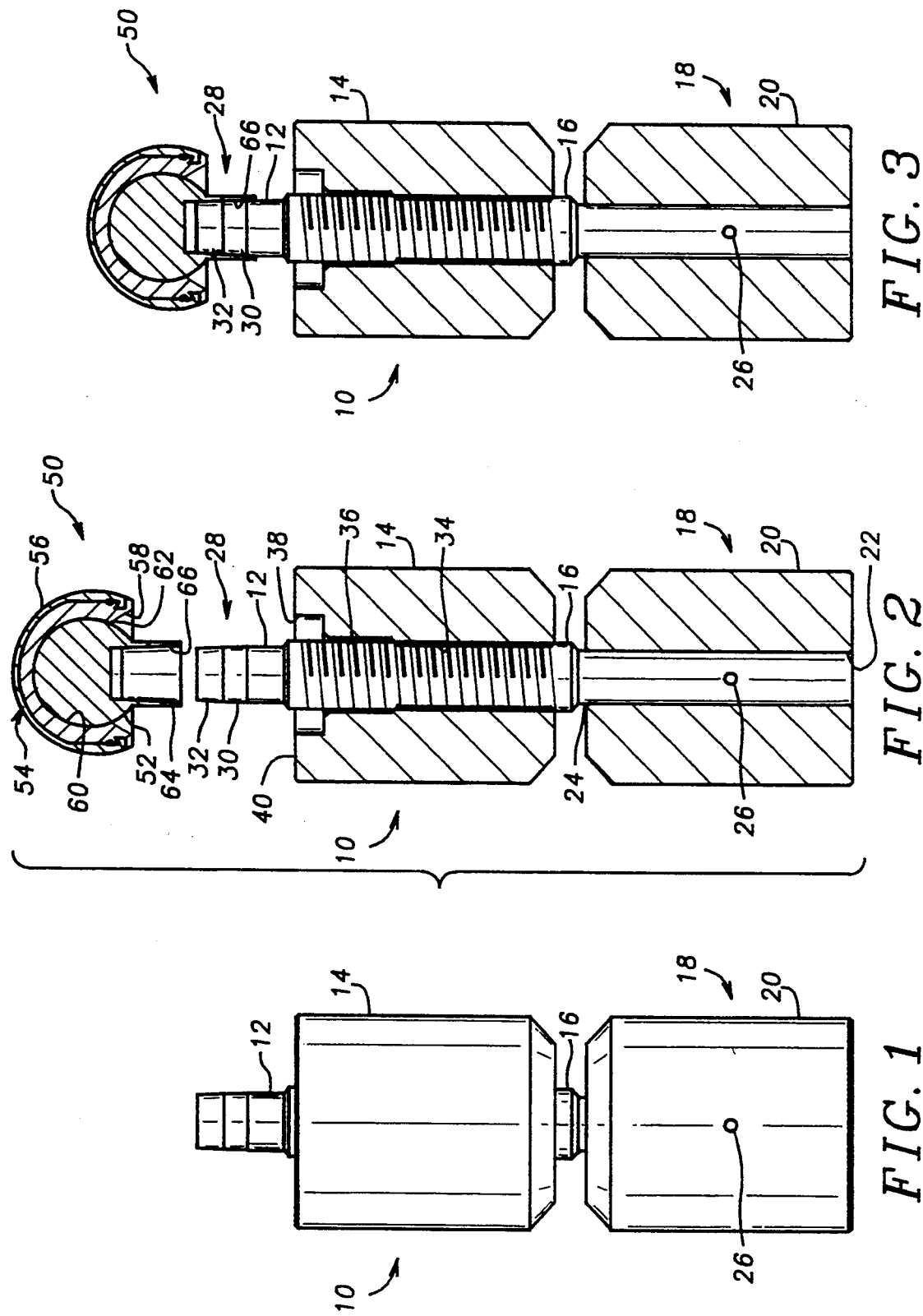

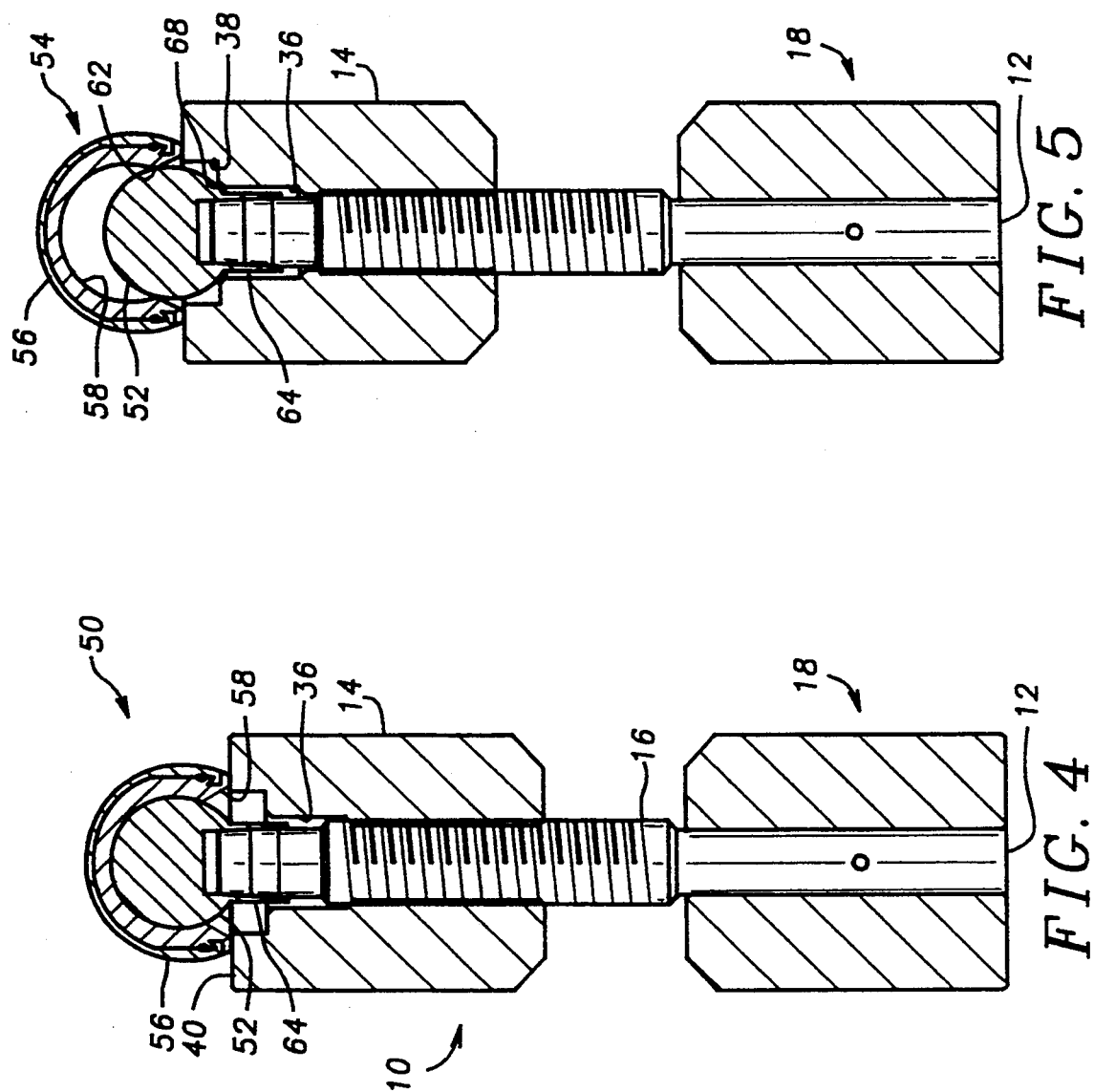

INSTRUMENT FOR DISASSEMBLING A BIPOLAR HIP PROSTHESIS

BACKGROUND OF THE INVENTION

1. Field of the Invention

The present invention relates generally to implantable orthopedic prostheses, and more particularly to an instrument for disassembling a head and acetabular component of a bipolar orthopedic hip prosthesis.

2. Background Information

One known configuration of an implantable hip prosthesis involves a femoral component having a stem for implantation in the proximal femur and a conically tapered neck on which is received a spherical head having a corresponding conically tapered bore. The male taper of the neck and the female taper of the head are selected to provide a taper locking interference fit when mutually engaged. An acetabular component is provided for use with the femoral component. The acetabular component can be of the type having an outer shell with a smooth, spherical outer surface for receipt within the natural acetabulum, and a bearing insert having a smooth, spherical inner surface for receiving the head of the femoral component. The outer shell is usually constructed of a biocompatible metal having a highly polished surface that moves freely within the natural acetabulum. The bearing insert is usually constructed of a biocompatible, low friction plastic material such as high density polyethylene. The smooth inner surface of the bearing insert moves freely relative to the femoral head. This type of acetabular component is sometimes referred to as a "bipolar" prosthesis due to the freedom of movement which exists between the femoral head and bearing insert, and between the smooth outer shell and the natural acetabulum.

To provide the implanting surgeon with maximum flexibility in fitting a bipolar hip prosthesis to a particular patient, the various components of the hip prosthesis are often provided in a range of sizes for selection and assembly at the time of implantation. For example, the femoral heads might be provided in a single diameter, but with the female taper disposed at various depths within the head to vary the offset of the head from the femoral stem. Furthermore, the acetabular components might be provided with an inner bearing diameter sized to match the common femoral head diameter, but with various diameters of the outer shell being available to match the patient's acetabulum. Because of the number of different possible combinations of femoral heads and acetabular components, it is preferred to assemble the selected head to the selected acetabular component at the time of implantation. The design of the bearing insert therefore requires that the femoral head can be inserted therein with relative ease, and yet be constrained therein against dislocation and separation under the forces to which the hip joint is commonly exposed.

One configuration for an acetabular component that permits ease of assembly and yet constrains the femoral head against separation involves a poly bearing insert that provides somewhat more than hemispherical coverage of the femoral head and that has an opening to the bearing cavity that is somewhat smaller in diameter than the diameter of the femoral head. Such a bearing insert undergoes temporary elastic deformation as the femoral head is forced into the bearing cavity, followed by a return to its initial configuration which provides constraint of the femoral head therein.

Occasionally, after the implanting surgeon has made an initial selection of a femoral head and an acetabular component and has assembled them together, it will subsequently be determined that a different component size would be preferable. In such situations it is desirable that appropriate instrumentation be available to disassemble the femoral head and acetabular component without risk of damage to the bearing insert or the highly polished surfaces of the femoral head and the outer shell.

SUMMARY IF THE INVENTION

In accordance with one aspect of the present invention, an apparatus for disassembling a head and acetabular component of a bipolar orthopedic hip prosthesis is provided. The head includes a female taper configured for engaging a corresponding male taper of a femoral component of a hip prosthesis, and the acetabular component includes a cavity in which the head is elastically constrained. The apparatus includes a rod having a male taper proximate one end thereof sized and configured to be received in taper locking engagement in the female taper of the head of the bipolar prosthesis. The rod has a threaded portion having external screw threads thereon. A sleeve surrounds at least a portion of the rod and has internal screw threads in threaded engagement with the external screw threads of the rod. The sleeve includes a thrust surface proximate one end thereof sized and configured to engage the acetabular component when moved theretoward while the head is in taper locked engagement with the male taper of the rod. Rotation of the sleeve relative to the rod causes the sleeve to advance axially toward the male taper whereupon the thrust surface engages the acetabular component and presses the acetabular component off of the head while the head remains taper locked to the rod.

It is an object of the present invention to provide an instrument for disassembling a head and acetabular component of a bipolar orthopedic hip prosthesis. Other objects and advantages of the present invention will be apparent from the following descriptions of a preferred embodiment, with reference to the drawings.

BRIEF DESCRIPTION OF THE DRAWINGS

FIG. 1 is an elevational view of an instrument for disassembling a femoral head and acetabular component of a bipolar prostheses constructed in accordance with the present invention.

FIG. 2 is a cross-sectional view of the instrument of FIG. 1 shown in a first configuration ready for use with a bipolar prosthesis shown in cross section.

FIG. 3 is a cross-sectional view of the instrument of FIG. 1 shown in a second configuration in taper locked engagement with the femoral head of the bipolar prosthesis.

FIG. 4 is a cross-sectional view of the instrument of FIG. 1 shown in a third configuration wherein the sleeve of the instrument has been moved into engagement with the acetabular component of the bipolar prosthesis.

FIG. 5 is a cross-sectional view of the instrument of FIG. 1 shown in a fourth configuration wherein the sleeve of the instrument has been moved so as to separate the acetabular component from the femoral head and the sleeve has moved into engagement with the femoral head of the bipolar prosthesis.

DESCRIPTION OF THE PREFERRED EMBODIMENT

Referring to FIGS. 1 and 2, there is illustrated a preferred embodiment of an instrument 10 constructed in accordance with the present invention. Instrument 10 includes two principal components: a rod 12 and a cylindrical sleeve 14 surrounding a portion of rod 12. Rod 12 also includes an externally threaded portion 16 and an enlarged diameter handle portion 18 which can be gripped for manipulating rod 12 and for preventing rotation of rod 12 during use, as will be described further below. More particularly, in the embodiment shown, handle portion 18 includes a cylindrical sleeve handle 20 having an axial bore 22 in which is received a handle portion 24 of rod 12 in relatively close fitting engagement. A transverse pin 26 is press-fitted through aligned bores in sleeve handle 20 and rod 12 such that sleeve handle 20 is fixed to rod 12 at the distal end thereof against relative axial or rotational movement.

Rod 12 also includes a male taper 28 at the proximal end thereof. More particularly, taper 28 includes first and second taper sections 30 and 32 having differing degrees of taper. Taper section 30, located distally of taper section 32, is conically tapered to a lesser degree than the proximal taper section 32. Taper section 30 tapers radially inwardly and in the proximal direction at an angle of about 2.5° relative to the longitudinal axis of rod 12. Taper section 32 tapers radially inwardly and in the proximal direction at an angle of about 2.8° relative to the longitudinal axis of rod 12. The dual tapered construction illustrated allows instrument 10 to be used with femoral heads having female tapers conforming to either one of the two taper angles.

Sleeve 14 includes an inner bore having an internally threaded distal portion 34 in threaded engagement with threaded portion 16 of rod 12, and having a smooth proximal portion 36 having an inner diameter sufficiently large to pass over the threads of threaded portion 16 without interference. Sleeve 14 also includes an enlarged bore 38 that communicates with bore 36 and is open at proximal end surface 40 of sleeve 14. Bore 38 has a diameter sufficiently large to avoid undesired interference with the underside of the femoral head with which instrument 10 is to be used, as described further below. Furthermore, bore 36 has a diameter sufficiently large to avoid undesired interference with the skirt 64, if any, of the femoral head with which instrument 10 is to be used.

Referring again to FIG. 2, there is shown together with instrument 10 a prior art bipolar hip prosthesis 50 including a spherical femoral head 52 constructed of biocompatible metal, and an acetabular component 54 including a spherical outer shell 56 constructed of biocompatible metal and a bearing insert 58 constructed of biocompatible plastic. Femoral head 52 and outer shell 56 preferably are constructed of a cobalt-chrome alloy, and the outer surface of each is provided with a high polish. Bearing insert 58 is preferably constructed of high density polyethylene, and includes a spherical cavity 60 in which femoral head 52 is received. Spherical cavity 60 provides somewhat more than hemispherical coverage of femoral head 52, and consequently has an opening 62 that is somewhat smaller in diameter than the diameter of femoral head 52. When femoral head 52 is pressed into cavity 60 of bearing insert 58, opening 62 temporarily deforms elastically as the maximum diameter of femoral head 52 passes therethrough. Opening 62 subsequently returns to its former dimensions to constrain femoral head 52 within cavity 60. Cavity 60 has a smooth surface which presents a low friction bearing surface to femoral head 52 for free articulation therewith. Femoral head 52 includes a cylindrical skirt 64 having an open female taper bore 66. Female taper 66 is sized and configured with respect to diameter and degree of taper to mate in taper locking engagement with a complementary male taper on a neck of a femoral stem (not shown), as is well known in the art. The degree of taper of female taper 66 corresponds to that of one or the other of male taper sections 30 and 32.

The depth of recess of female taper bore 66 within femoral head 52 is selectable to provide a particular offset of the femoral head 52 from the femoral stem. Where female taper bore 66 is deeply recessed, skirt 64 is omitted from femoral head 52. Where female taper bore 66 is shallowly recessed, skirt 64 is provided to surround that portion of female taper bore 66 that extends outwardly from the spherical portion of femoral head 52.

Referring in particular to FIGS. 3–5, instrument 10 is shown in use. In FIG. 3, bipolar hip prosthesis 50 has been seated on taper 28 of rod 12, such that there is a taper lock interference fit between one or the other of tapers 30 and 32 and female taper bore 66. It is important to the operation of instrument 10 that bipolar hip prosthesis 50 be firmly seated on rod 12 because the taper locked engagement will be placed in tension during use of the instrument and the taper lock must not disengage prematurely. Thus, it is recommended that instrument 10 be stood upright on a flat, well supported surface, and that bipolar hip prosthesis 50 be assembled to instrument 10 such that taper 28 is within taper bore 66. An appropriate impactor tool having a surface that will not mar outer shell 56 is held above the assembly in contact with bipolar hip prosthesis 50. Two medium-force blows from a mallet against the impactor tool cause the respective male and female tapers to interlock. Secure engagement can be verified by manually pulling the bipolar hip prosthesis.

In FIG. 4, threaded sleeve 14 has been rotated relative to threaded portion 16 of rod 12 so as to be advanced axially by the threaded engagement of sleeve 14 with rod 12. This can be accomplished by holding rod 12 in one hand by handle 18, and rotating sleeve 14 relative to handle 18 until thrust surface 40 of sleeve engages the undersurface of bipolar hip prosthesis 50. More particularly, thrust surface 40 engages and imparts axial thrust to polyethylene insert 58. Note that in FIG. 4 there is no interference or contact between instrument 10 and femoral head 52 or skirt 64. Bore 36 of sleeve 14 is of sufficient diameter and depth to clear skirt 64 as sleeve 14 is advanced axially in the distal direction, i.e., toward bipolar hip prosthesis 50.

Referring to FIG. 5, sleeve 14 has been advanced farther so as to press off acetabular component 54 comprised of shell 56 and insert 58 and disengage it from femoral head 52. As acetabular component 54 is pressed off, opening 62 of insert 58 temporarily deforms elastically as the maximum diameter of femoral head 52 passes therethrough. Opening 62 subsequently returns to its former dimensions, without damage, as shown in FIG. 5. It should be understood that the amount of force required to disengage the taper lock between taper 28 of rod 12 and taper bore 66 of femoral head 52 is greater than the amount of force necessary to deform insert 58 and disengage acetabular component 54 from femoral head 52. As acetabular component 54 becomes disengaged from femoral head 52, femoral head 52 remains firmly locked to rod 12. As sleeve 14 continues to be rotated and moved axially, chamfer 68, at the junction of bore 36 and bore 38 of sleeve 14, comprises a thrust surface that engages the spherical undersurface of femoral head 52, as shown in FIG. 5. At this point, acetabular component 54 is completely disengaged and is manually removed to avoid its being dropped and damaged. By continuing to rotate sleeve 14 farther, pressing force is imparted by chamfer 68 to femoral head 52 until the applied force is sufficient to disengage the taper lock between femoral head 52 and rod 12, at which time femoral head 52 is manually removed from instrument 10. The pressing force on femoral head 52 is applied evenly along the annular engagement between annular chamfer 68 and head 52. The angle of chamfer 68 is chosen to present a contact surface that is approximately tangent to the spherical undersurface of femoral head 52 so as not to mar the polished surface of head 52. There is no contact between the wall of bore 36 and skirt 64, nor is there contact between the wall of bore 38 and head 52. Sleeve 14 is preferably constructed of acetal copolymer plastic, which has sufficient rigidity to withstand the forces imparted, but is of lesser hardness than the material of which head 52 is constructed, thereby avoiding scratching of head 52 as sleeve 14 is rotated against it. Even if minor scratching were to occur, it would not present a serious problem since chamfer 68 contacts the undersurface of femoral head 52 in a noncritical area. It is also preferred that handle 18 be constructed of acetal copolymer plastic to reduce the weight of the tool, but material is not critical to its construction and other materials can be used as desired so long as they provide sufficient strength to serve the purpose of handle 18, which is to provide a convenient gripping surface and to impart torque to rod 12 as sleeve 14 is rotated.

While the present invention has been illustrated and described with particularity in terms of a preferred embodiment, it should be understood that no limitation of the scope of the invention is intended thereby. The scope of the invention is defined only by the claims appended hereto. It should also be understood that variations of the particular embodiment described herein incorporating the principles of the present invention will occur to those of ordinary skill in the art and yet be within the scope of the appended claims.

What is claimed is:

1. A prosthetic system an assembled head and acetabular component of a bipolar orthopedic hip prosthesis, said head including a female taper configured for engaging a corresponding male taper of a femoral component of a hip prosthesis in self-locking taper locked engagement, and said acetabular component including a cavity in which said head is elastically constrained, and means for disassembling said assembled head and acetabular component including:

means for engaging said head of said bipolar prosthesis including a rod having a male taper proximate one end thereof receivable in self-locking taper locked engagement in the female taper of said head of said bipolar prosthesis, said rod having a threaded portion having external screw threads thereon; and means for engaging said acetabular component of said bipolar prosthesis including a sleeve surrounding at least a portion of said rod and having internal screw threads in threaded engagement with the external screw threads of said rod, said sleeve including a thrust surface proximate one end thereof engagable with said acetabular component when moved theretoward while said head is in taper locked engagement with said male taper of said rod;

wherein rotation of said sleeve relative to said rod causes said sleeve to advance axially toward said male taper whereupon said thrust surface engages said acetabular component and presses said acetabular component off of said head while said head remains taper locked to said rod.

2. The prosthetic system of claim 1, in which said rod further includes a handle portion sized and configured to be gripped to prevent said rod from rotating when said sleeve is rotated.

3. The prosthetic system of claim 1, in which said thrust surface is further sized and configured to initially engage said acetabular component when moved theretoward and upon further movement to subsequently engage said head, such that said acetabular component is firstly disengaged from said head and said head is secondly disengaged from said male taper.

4. The prosthetic system of claim 3, in which said thrust surface includes a first annular portion having an inner diameter large enough to avoid contact with said head while contacting said acetabular component, and a second annular thrust surface having an inner diameter sized to contact said head on a spherical undersurface thereof.

5. The prosthetic system of claim 4, in which said second annular thrust surface is displaced axially from said first annular portion.

6. The prosthetic system of claim 5, in which said second annular thrust surface includes an annular chamfer having a chamfer angle selected such that said chamfer engages said spherical undersurface of said head approximately tangentially thereto to avoid marring said spherical undersurface.

7. The prosthetic system apparatus of claim 4, in which said head has a cylindrical skirt surrounding said female taper, and said second annular thrust surface has an inner diameter large enough to avoid contact with said skirt of said head while contacting a spherical undersurface of said head.

8. The apparatus of claim 1, in which said male taper includes first and second taper sections having different degrees of taper.

* * * * *

UNITED STATES PATENT AND TRADEMARK OFFICE
CERTIFICATE OF CORRECTION

PATENT NO. : 5,405,404
DATED : April 11, 1995
INVENTOR(S) : Gardner et al.

It is certified that error appears in the above-identified patent and that said Letters Patent is hereby corrected as shown below:

Column 5, line 50, after "1. A prosthetic system" insert --comprising:--.
Column 6, line 51, delete "apparatus"; line 57, delete "apparatus" and substitute therefor --prosthetic system--.

Signed and Sealed this

Fourth Day of July, 1995

Attest:

BRUCE LEHMAN

Attesting Officer

Commissioner of Patents and Trademarks